US012746592B2

(12) United States Patent
Greenberg et al.

(10) Patent No.: US 12,746,592 B2
(45) Date of Patent: Sep. 29, 2026

(54) NEEDLE BENDING DEVICE

(71) Applicant: Precision Bend LLC, Verona, WI (US)

(72) Inventors: Jared Greenberg, Verona, WI (US); Alan Pitas, Evansville, WI (US)

(73) Assignee: Precision Bend LLC, Verona, WI (US)

( * ) Notice: Subject to any disclaimer, the term of this patent is extended or adjusted under 35 U.S.C. 154(b) by 717 days.

(21) Appl. No.: 18/245,952

(22) PCT Filed: Sep. 15, 2021

(86) PCT No.: PCT/US2021/050381
§ 371 (c)(1),
(2) Date: Mar. 20, 2023

(87) PCT Pub. No.: WO2022/060778
PCT Pub. Date: Mar. 24, 2022

(65) Prior Publication Data

US 2023/0381851 A1 Nov. 30, 2023

Related U.S. Application Data

(60) Provisional application No. 63/081,059, filed on Sep. 21, 2020.

(51) Int. Cl.
*B21F 1/00* (2006.01)
*A61B 17/00* (2006.01)
*A61B 17/34* (2006.01)

(52) U.S. Cl.
CPC .......... *B21F 1/002* (2013.01); *A61B 17/3401* (2013.01); *A61B 2017/00526* (2013.01)

(58) Field of Classification Search
CPC ........ A61M 25/0625; A61M 2005/325; A61M 5/3273; A61M 5/3243; A61M 5/3257;
(Continued)

(56) References Cited

U.S. PATENT DOCUMENTS 3,712,302 A * 1/1973 Burke ................. A61M 5/3213
604/110
4,266,544 A * 5/1981 Wardlaw ................. A61M 5/50
604/110

(Continued)

FOREIGN PATENT DOCUMENTS

CN 202894153 4/2013
DE 102017110619 11/2018

(Continued)

OTHER PUBLICATIONS

Extended European Search Report for European Application No. 21870098.7, mailed Sep. 23, 2024, 8 Pages.

(Continued)

*Primary Examiner* — Cris L. Rodriguez
(74) *Attorney, Agent, or Firm* — Casimir Jones, S.C.; Peter J. Schlueter

(57) ABSTRACT

Provided herein are devices, systems, and methods for bending a needle. More particularly, the present disclosure provides materials and methods relating to bending the distal end of a needle with more precision than conventional means, which improves the performance of various medical procedures and leads to better patient outcomes.

21 Claims, 16 Drawing Sheets

(58) Field of Classification Search
CPC .......... A61M 25/0618; A61M 25/0631; A61M 25/0637; A61M 5/3213; A61M 5/3205; A61M 5/002; A61M 2005/3284; A61M 2205/581; A61M 5/5086; A61M 5/3278; B21F 1/002; A61B 17/3401; A61B 2017/00526
USPC ................. 600/573, 576–584; 206/365, 364; 225/940, 93, 104; 83/944
See application file for complete search history.

(56) References Cited

U.S. PATENT DOCUMENTS

| | | | | | | |
|---|---|---|---|---|---|---|
| 4,332,323 | A | * | 6/1982 | Reenstierna | A61M 5/3213 604/110 |
| 5,066,279 | A | * | 11/1991 | Russell | A61M 5/3213 604/110 |
| 5,158,550 | A | * | 10/1992 | Scholl, Jr. | A61M 5/3205 604/110 |
| 5,201,210 | A | * | 4/1993 | Stein, III | B21G 1/08 72/457 |
| 5,554,126 | A | | 9/1996 | Filley | |
| 5,554,129 | A | * | 9/1996 | Stevenson | A61M 5/3213 604/110 |
| 5,810,784 | A | * | 9/1998 | Tamaro | A61M 5/3275 604/263 |
| 5,816,095 | A | | 10/1998 | Nordell et al. | |
| 6,761,705 | B1 | * | 7/2004 | Chiu | A61M 5/3243 604/110 |
| 9,561,053 | B2 | | 2/2017 | Bonde et al. | |
| 9,901,705 | B2 | | 2/2018 | Armour et al. | |
| 11,014,141 | B1 | * | 5/2021 | Parazynski | B21G 1/08 |
| 2005/0203459 | A1 | * | 9/2005 | Alchas | A61M 5/46 604/117 |
| 2011/0224626 | A1 | | 9/2011 | Lin et al. | |
| 2012/0051967 | A1 | * | 3/2012 | Murphy | A61M 5/002 422/28 |
| 2014/0196517 | A1 | | 7/2014 | Peterson | |
| 2014/0221924 | A1 | * | 8/2014 | Hiles | A61M 5/50 604/110 |
| 2018/0280629 | A1 | | 10/2018 | Tuttle | |
| 2018/0296799 | A1 | | 10/2018 | Horst et al. | |
| 2020/0038054 | A1 | | 2/2020 | Yim | |
| 2023/0034291 | A1 | * | 2/2023 | Panjeton | B21G 1/08 |
| 2023/0381846 | A1 | * | 11/2023 | Parazynski | B21D 7/024 |
| 2024/0148984 | A1 | * | 5/2024 | McCarty | A61M 5/3286 |

FOREIGN PATENT DOCUMENTS

| | | | | | |
|---|---|---|---|---|---|
| KR | 200482477 | | | 2/2017 | |
| WO | WO-0056384 | A1 | * | 9/2000 | A61M 5/322 |
| WO | WO-0178806 | A1 | * | 10/2001 | A61M 5/3205 |
| WO | WO-2021127645 | A1 | | 6/2021 | |

OTHER PUBLICATIONS

International Search Report and Written Opinion for PCT/US2021/050381. Mailed Dec. 20, 2021. 10 pages.

* cited by examiner

NEEDLE BENDING DEVICE

CROSS REFERENCE TO RELATED APPLICATIONS

This application claims priority to and the benefit of U.S. Provisional Patent Application No. 63/081,059 filed Sep. 21, 2020, which is incorporated herein by reference in its entirety for all purposes.

FIELD

Provided herein are devices, systems, and methods for bending a needle. More particularly, the present disclosure provides materials and methods relating to bending a distal end of a needle with more precision than conventional means, which improves the performance of various medical procedures and leads to better patient outcomes.

BACKGROUND

Fine-gauge needles are commonly used to reduce unwanted side-effects of large gauge needles. For example, with respect to performing a medical procedure, a fine-gauge spinal needle is used to reduce puncture headaches. However, fine-gauge needles can be associated with increased risk of placement failure as a result of deflection that occurs while performing a medical procedure. Needle deflections are primarily attributed to unbalanced force interactions at the tip of the needle during insertion into or through tissue (s). Medical professionals utilize needle bending to offset needle deflection, thereby facilitating better control of needle placement. Since needle bending is commonly done manually by the medical professional just prior to performing a medical procedure, it is often imprecise and not reproducible. Although pre-bent needles are available, they are typically limited to those having bend angles that are mass-produced, which does not allow for a customized bend that takes into account important factors for performing a medical procedure, such as the nature of the procedure or patient characteristics.

SUMMARY

Embodiments of the present disclosure include a needle bending device, and related methods of bending a needle for therapeutic purposes. In accordance with these embodiments, the device includes a base, a hollow slider conduit, and a bending element.

In some embodiments, the base comprises a needle hub housing at a proximal end of a shaft.

In some embodiments, the needle hub housing is configured to receive a needle and engage a needle hub.

In some embodiments, the shaft comprises an elongated internal chamber configured to receive the hollow slider conduit from a distal end.

In some embodiments, the elongated internal chamber comprises one or more grooves on an interior surface to receive one or more ridges on an exterior surface of the hollow slider conduit.

In some embodiments, the hollow slider conduit has an open distal end. In some embodiments, the hollow slider conduit has a closed distal end comprising an aperture. In some embodiments, the hollow slider conduit comprises a slot running parallel along the length of the hollow slider conduit and perpendicular from the exterior surface to an internal chamber of slider conduit. In some embodiments, the hollow slider conduit comprises a notch on the exterior surface proximal to the bending element. In some embodiments, the hollow slider conduit comprises a hinged flap configured to be received in the notch.

In some embodiments, the device further comprising a press.

In some embodiments, the hollow slider conduit comprises a fulcrum.

In some embodiments, the bending element engages with the hollow slider conduit at a distal end.

In some embodiments, the bending element is fully or partially transparent or semi-transparent. In some embodiments, the bending element comprises an opening. In some embodiments, the bending element comprises an indication of bend angle. In some embodiments, the indication corresponds to a bend angle of less than or equal to 30 degrees. In some embodiments, the indication corresponds to a bend angle of about 5 degrees.

In some embodiments, the device further comprises a clamp attached to the slider conduit. In some embodiments, the clamp comprises a clamping element that engages the needle and holds the needle in a substantially secure position. In some embodiments, the clamp comprises a latching mechanism that allows the clamp to engage the slider conduit and hold the clamp in a substantially secure position. In some embodiments, the clamp is detachably coupled to the slider conduit.

In some embodiments, the slider conduit comprises a flange that prevents unintentional release of the slider conduit from the shaft.

In some embodiments, the device further comprises a needle. In some embodiments, the needle comprises a gauge ranging from about 20 to about 26. In some embodiments, the needle is 2 to 6 inches long. In some embodiments, the needle is a spinal needle.

Embodiments of the present disclosure also include a kit comprising any of the devices described herein, a needle, and a container.

In some embodiments, the needle comprises a gauge ranging from about 20 to about 26. In some embodiments, the needle is 2 to 6 inches long. In some embodiments, the needle is a spinal needle.

In some embodiments, the kit further comprises a syringe.

Embodiments of the present disclosure also include a method for bending a needle using any of the devices described herein.

In some embodiments, the bending comprises actuating the needle bending element to a desired needle bend angle. In some embodiments, the desired needle bend angle is less than or equal to 30 degrees.

In some embodiments, the method comprises positioning the hollow slider conduit within the base, and positioning the needle bending element over at least a portion of the hollow slider conduit at a distal end.

In some embodiments, the method comprises positioning a clamp on the exterior surface of the slider conduit proximal to the bending element.

In some embodiments, the method comprises inserting the needle into the base, and securing a needle hub in the needle hub housing.

In some embodiments, the method comprises positioning the clamp such that it engages and secures the needle, and comprises applying pressure to the bending element to create a bend in the distal end of the needle.

In some embodiments, the method comprises disengaging needle from the needle bending element, the hollow slider conduit, and the base, simultaneously or sequentially.

Definitions

To facilitate understanding of the invention, a number of terms are defined below.

"Fulcrum," as used herein, refers to the point or structure which provides the pivot point for the bend being introduced in the needle.

A "needle" refers to any medically relevant needle which is hollow, having a needle lumen, and usually comprises a bevel on the needle tip. The needle may be a hypodermic needle, a dialysis needle, a huber needle, and a spinal needle.

A needle "gauge" refers to the diameter of a needle. Different gauge systems are known in the art. For purposes of referring to specific dimensions, the numerical gauge values provided herein employ the Birmingham gauge (also known as the Stubs Iron Wire Gauge or Birmingham Wire Gauge). Table 1 below provides internal and external diameter values for some exemplary needle gauges. The device may be used with any gauge of needle, with a preference for finer or higher gauge needles. In some embodiments, the gauge is between 22 and 26.

TABLE 1

Inner and outer diameter for representative needle gauges

| Gauge | Nominal outer diameter (mm) | Nominal inner diameter (mm) |
|---|---|---|
| 16 | 1.651 (+/−0.013) | 1.194 (+/−0.038) |
| 18 | 1.270 (+/−0.013) | 0.838 (+/−0.038) |
| 20 | 0.9081 (+/−0.0064) | 0.686 (+/−0.019) |
| 22 | 0.7176 (+/−0.0064) | 0.413 (+/−0.019) |
| 24 | 0.5652 (+/−0.0064) | 0.311 (+/−0.019) |
| 26 | 0.4636 (+/−0.0064) | 0.260 (+/−0.019) |
| 28 | 0.3620 (+/−0.0064) | 0.184 (+/−0.019) |
| 30 | 0.3112 (+/−0.0064) | 0.159 (+/−0.019) |
| 32 | 0.2350 (+/−0.0064) | 0.108 (+/−0.019) |
| 34 | 0.1842 (+/−0.0064) | 0.0826 (+/−0.019) |

A "syringe" is a device comprising a barrel, typically but not necessarily tube-shaped, for injecting or withdrawing a sample in a thin stream, typically through a hollow needle. Samples are injected or withdrawn via pressure, typically from a reciprocating pump (e.g., employing a piston or plunger). A plunger can be linearly pulled and pushed along the inside of the barrel, allowing the syringe to take in and expel liquid or gas through a discharge orifice at the front (open) end of the tube. Syringes are fitted onto a needle at the needle hub.

BRIEF DESCRIPTION OF THE DRAWINGS

FIG. 9A is an exemplary slider conduit comprising a slot running lengthwise along the conduit between the outer surface of the slider conduit and the internal chamber. In FIG. 9B the slider conduit comprises a notch in the outer surface. The notch may be configured to receive a press or a hinged flap connected to the slider conduit.

FIGS. 10A and 10B provide perspective views of the distal end of the device, including the clamp and bending element. FIGS. 10C and 10D provide side views of the clamp in an engaged (FIG. 10C) or disengaged (FIG. 10D) position, which obviates the need for finger pressure.

FIG. 11A shows that a force of 0.01 N applied to the needle tip causes a deformation of 2.37 mm, while FIG. 11B shows that a force of 6,400,000 N/m of stress occurs at the base of the slider when the strain is set at 2.3 mm.

FIG. 12A provides a perspective side view of the distal end of the device that includes the clamp in a partially disengaged position, while FIG. 12B provides a perspective side view of the clamp in an engaged position.

FIG. 13A provides a side view of the flange prior to full engagement with the distal end of the shaft (double arrows), while FIG. 13B provides a side view of the flange fully engaged against the distal end of the shaft.

DETAILED DESCRIPTION

Illustrative embodiments of the invention are shown in the figures. It should be understood that the invention is not limited to these particular examples.

Devices of the present disclosure can be used to bend a needle at different, user-selectable locations along the length of the needle and user-selectable angles. For example, the devices of the present disclosure can be used to bend a distal portion of a needle to an angle that is equal to or less than 30 degrees without damaging the needle lumen. The components of the devices may be made of any suitable material, including, but not limited to, metals, metal alloys, plastics, glass, ceramics, polymeric materials, and any combinations thereof. In some cases, the materials are non-allergenic and sterilizable. The devices and methods described herein can find use in any context in which a medical procedure is performed, including research and clinical, e.g., surgical and therapeutic, settings.

Embodiments of the devices, systems, and methods of the present disclosure provide the ability to customize a needle for any therapeutic and/or medical use. For example, thin needles, which are ideally suited to decrease the size of a puncture, do not travel in a straight path when inserted into dense tissue resulting in undesired placement of the needle tip. For example, fine-gauge spinal needles are commonly used to reduce puncture headaches of large gauge needles but have increased risk of deflection while passing through tissue due to the finer gauge. The devices disclosed herein allow customized needle bends, which improve the maneuverability and physician control for quicker and more precise needle placement into the target structure or area thereby decreasing the chance of injury or complication (e.g., bleeding).

Figure 1A:
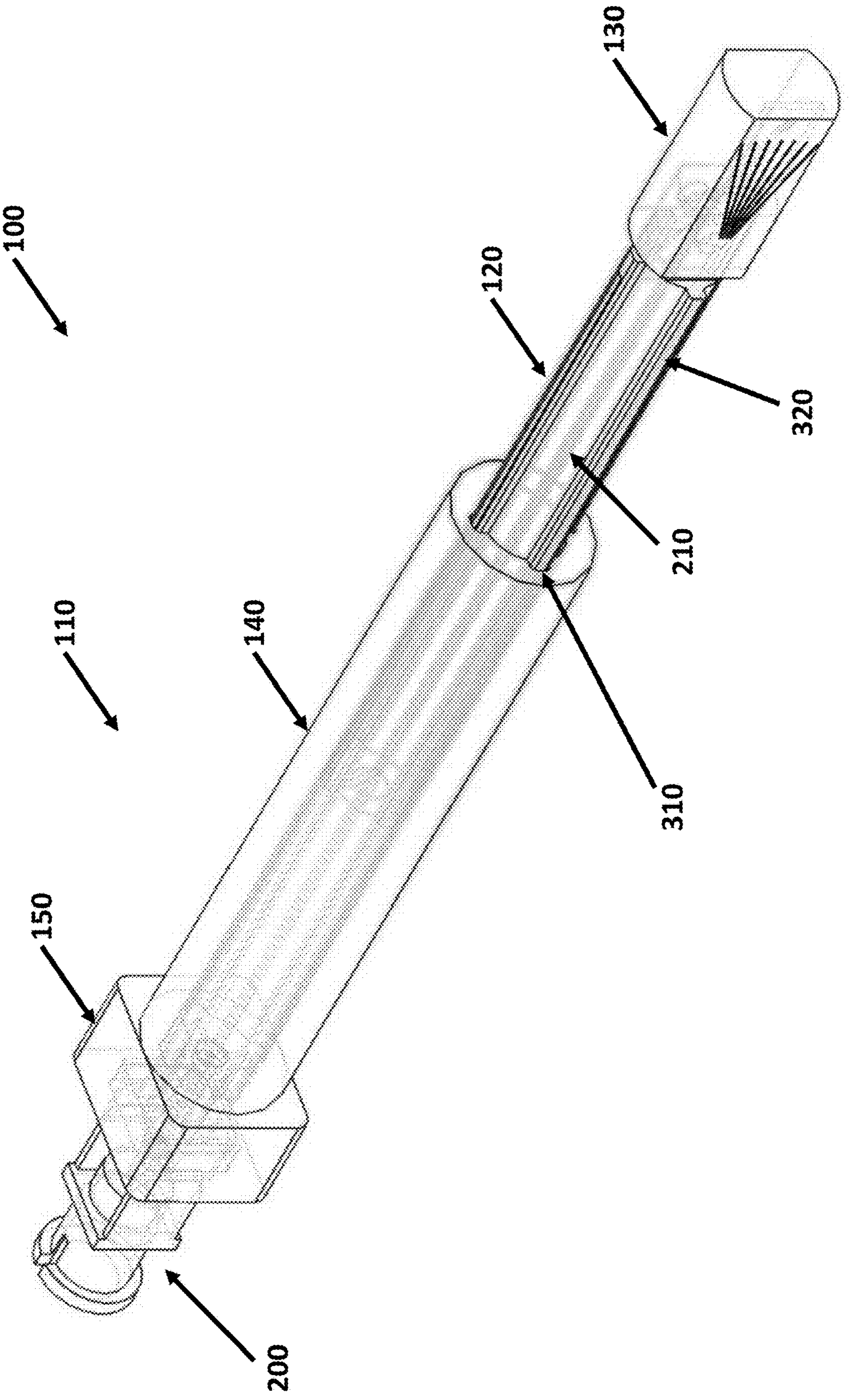
FIGS. 1A-1C show alternative views of an exemplary needle bending device comprising a base, a slider conduit, and a bending element comprising a needle, according to one embodiment of the present disclosure.
Figure 1B:
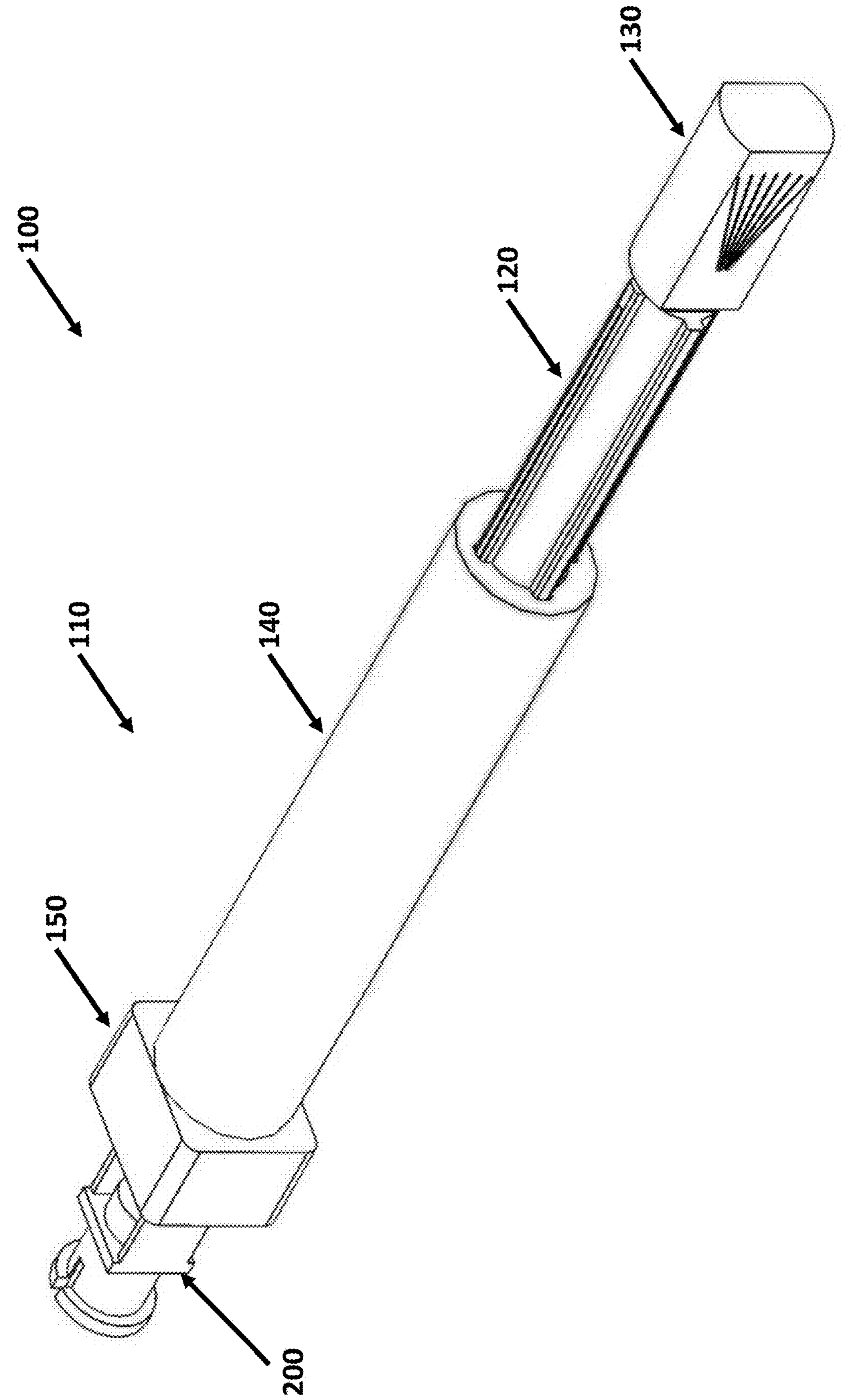
Figure 1C:
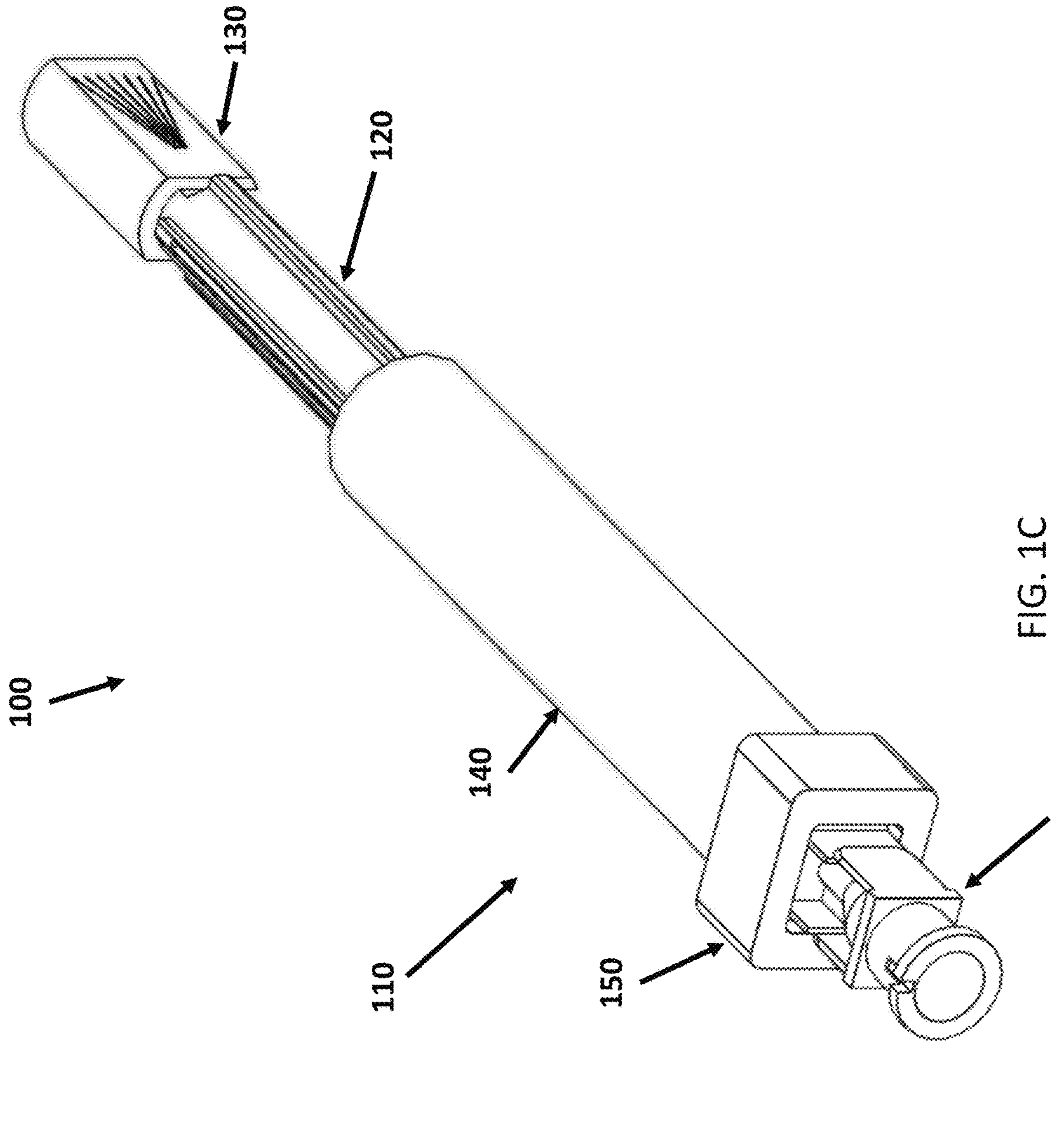
Figure 2A:
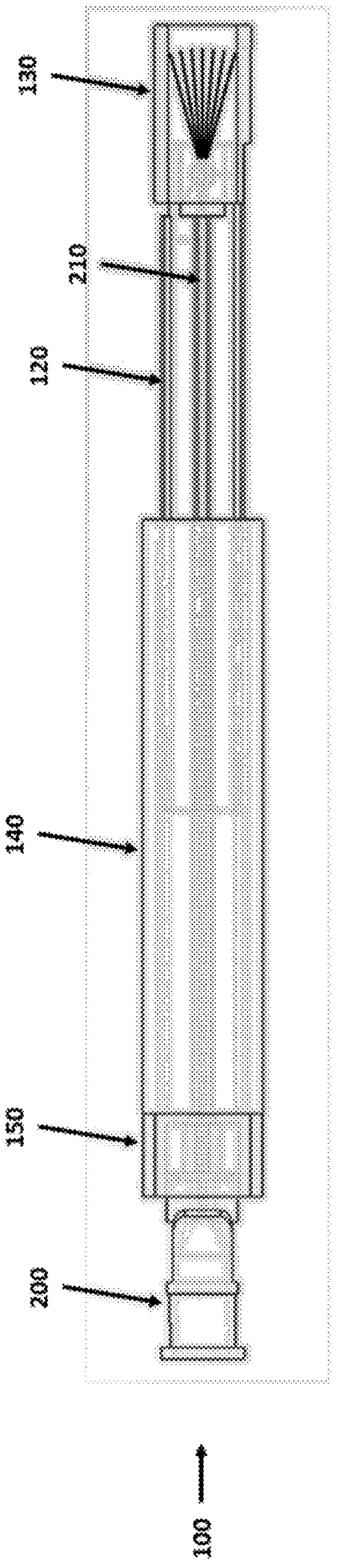
FIGS. 2A-2B show alternative views of an exemplary needle bending device comprising a base, a slider conduit, and a bending element mounted on a needle, according to one embodiment of the present disclosure.
Figure 2B:
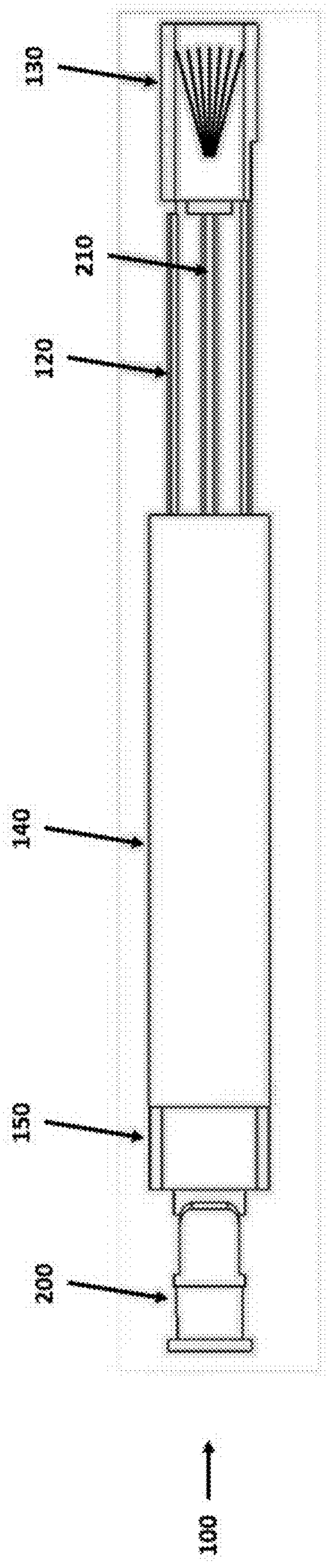

An exemplary device is shown in FIGS. 1A-1C. The needle bending device 100 comprises base 110, hollow slider conduit 120, and bending element 130. The device may, in some instances, further comprise a needle 210 having needle hub 200. Base 110 comprises needle hub housing 150 on a proximal end of shaft 140. Needle hub housing 150 is configured to receive needle 210 and engage with needle hub 200. The alignment of needle hub 200 in needle hub housing 150 is indicative of needle tip bevel angle and, as such, controls the orientation of the needle bend to the bevel (e.g., with or away from bevel).

Base shaft 140 comprises an elongated internal chamber 300 (FIG. 4) adapted to receive hollow slider conduit 120 from the distal end and allow passage of needle 210. The internal chambers of both the base shaft 140 and slider conduit 120 are of wide enough diameter to allow passage of a needle following bending, such that the bend will not be removed upon disengaging the needle from the device 100. The external and internal dimensions of base shaft 140 and slider conduit 120 are selected to house a number of different gauges of needles and for usability and convenience.

In some embodiments, the interior surface of elongated chamber 300 comprises at least one groove 310 (FIG. 4) to receive one or more ridges 320 (FIG. 5) on the outer surface of slider conduit 120. Slider conduit 120 may move longitudinally within the elongated chamber of the base shaft 140 along grooves 310 to accommodate needles of any length and allow customizable positioning of the bend. The device can be used with any needle length ranging from 2 to 6 inches. For example, a spinal needle is commonly 3.5 inches in length.

Figure 3A:
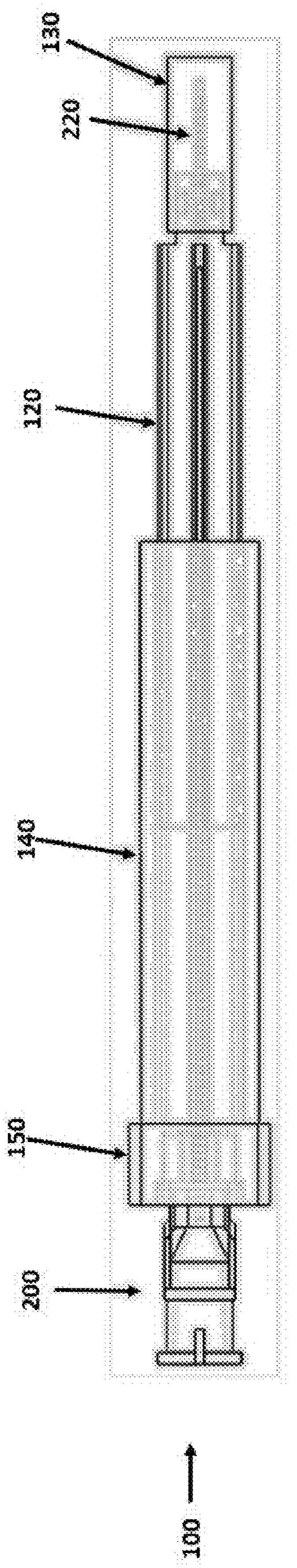
FIGS. 3A-3B show alternative views of an exemplary needle bending device comprising a base, a slider conduit, and a bending element mounted on a needle, according to one embodiment of the present disclosure.
Figure 3B:
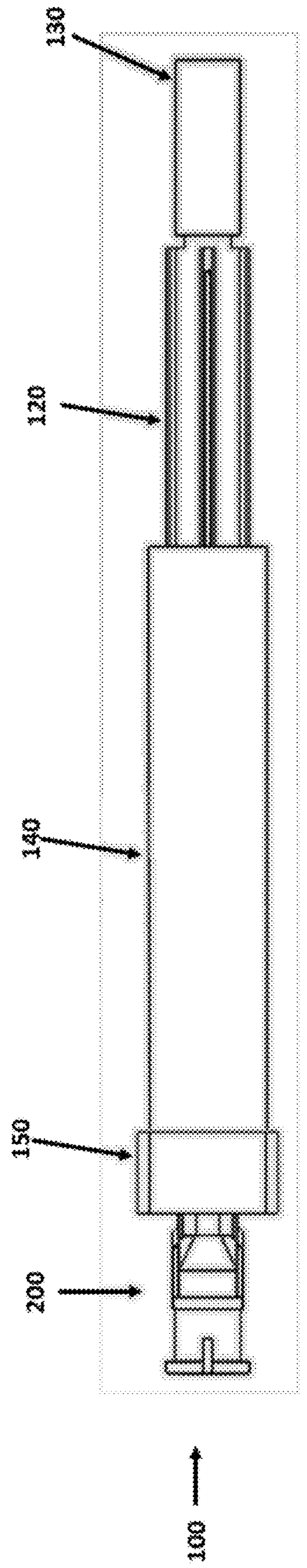
Figure 7:
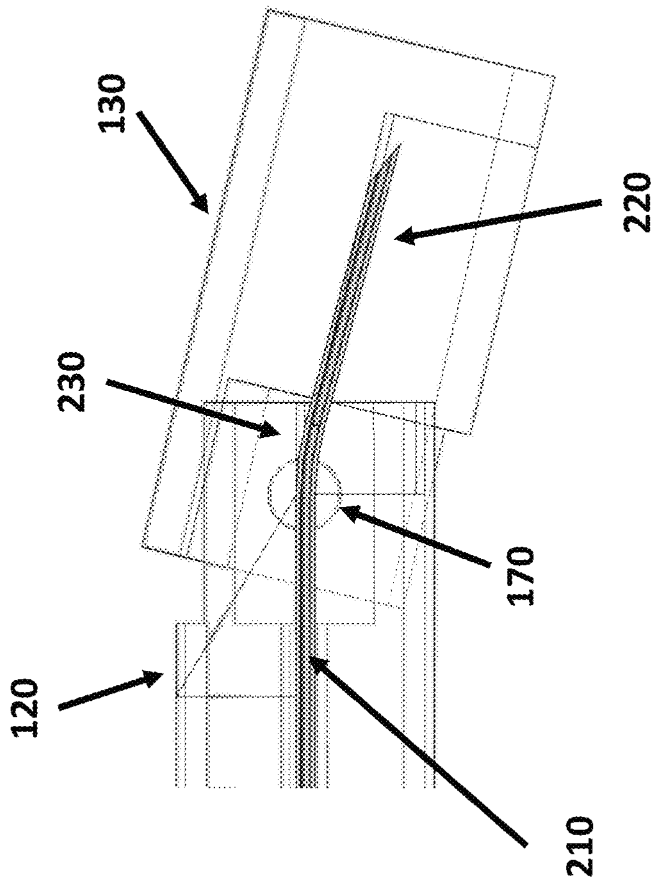
FIG. 7 shows engagement of an exemplary bending element and slider conduit during or after a needle bending process, according to one embodiment of the present disclosure.

Aperture 160 (FIG. 5) at the distal end of slider conduit 120 allows needle tip 220 to extend beyond the end of slider conduit 120 and into bending element 130, as shown in FIG. 3A and FIG. 7. The distal end of slider conduit 120 engages with bending element 130 such that actuating bending element 130 in a lateral arc movement results in bending of needle 210 at fulcrum 170. Thus, the user can easily bend needle 210 to a desired configuration or angle by applying pressure to bending element 130 which in turn applies pressure to the portion of the needle remaining outside slider conduit 120 at fulcrum 170. By conforming needle 210 to fulcrum 170, the user can bend needle 210 to a desired angle. Throughout the bending process, needle tip 220 is confined within the walls of the bending element 130 and the remaining portion of the shaft of needle 210 is protected and stabilized within the internal chambers of base shaft 140 and slider conduit 120.

The location of the bend is dictated by the position of needle 210 about fulcrum 170 and may be varied by moving slider conduit 120 longitudinally within the elongated chamber of the base shaft 140, as described above. Commonly the bend is positioned in the distal half of the needle, within a few centimeters of the tip. For example, in a 3.5 inch spinal needle bends are commonly positioned in the range of the distal 1 cm+/−0.5 cm of the needle.

FIGS. 2A-2B and FIGS. 3A-3B show alternative views of exemplary embodiments of the devices of the present disclosure with differing needle hub housings 150. Needle hub housing 150 may be configured to receive different needle hub 200 designs as used by different commercial suppliers of needles.

Figure 4:
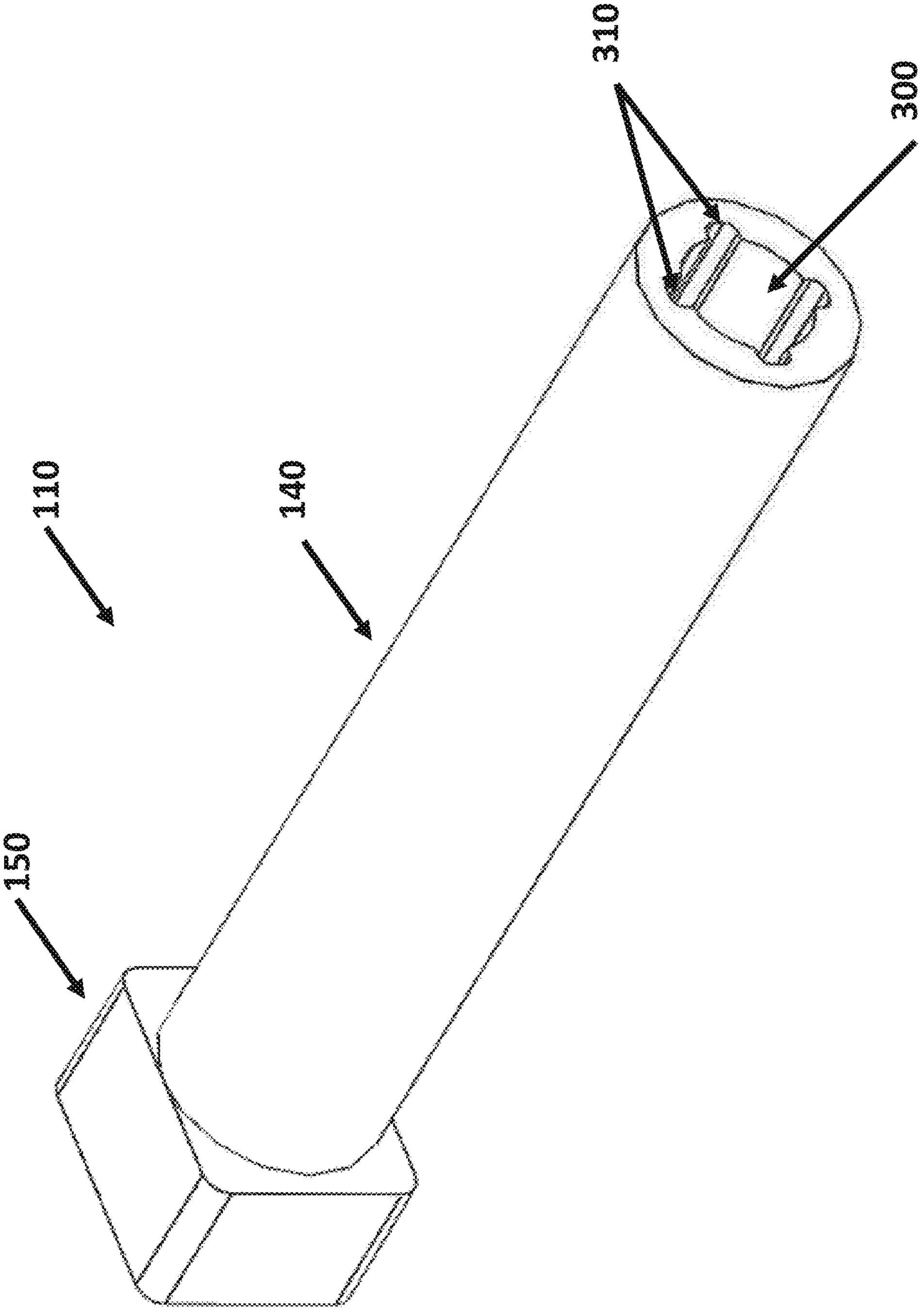
FIG. 4 shows an exemplary base of a needle bending device, according to one embodiment of the present disclosure.

FIG. 4 shows an exemplary embodiment of a base 110 comprising a needle hub housing 150 on a proximal end of shaft 140. In this embodiment, base shaft 140 has an elongated internal chamber 300, the interior surface of which comprises a plurality of grooves 310 to orientate and support the slider conduit 120. The internal dimension of the base shaft 140 is designed to encompass the slider conduit 120 and allow needles of a variety of gauges to be disengaged following bending in such a manner to retain the bend.

Figure 5:
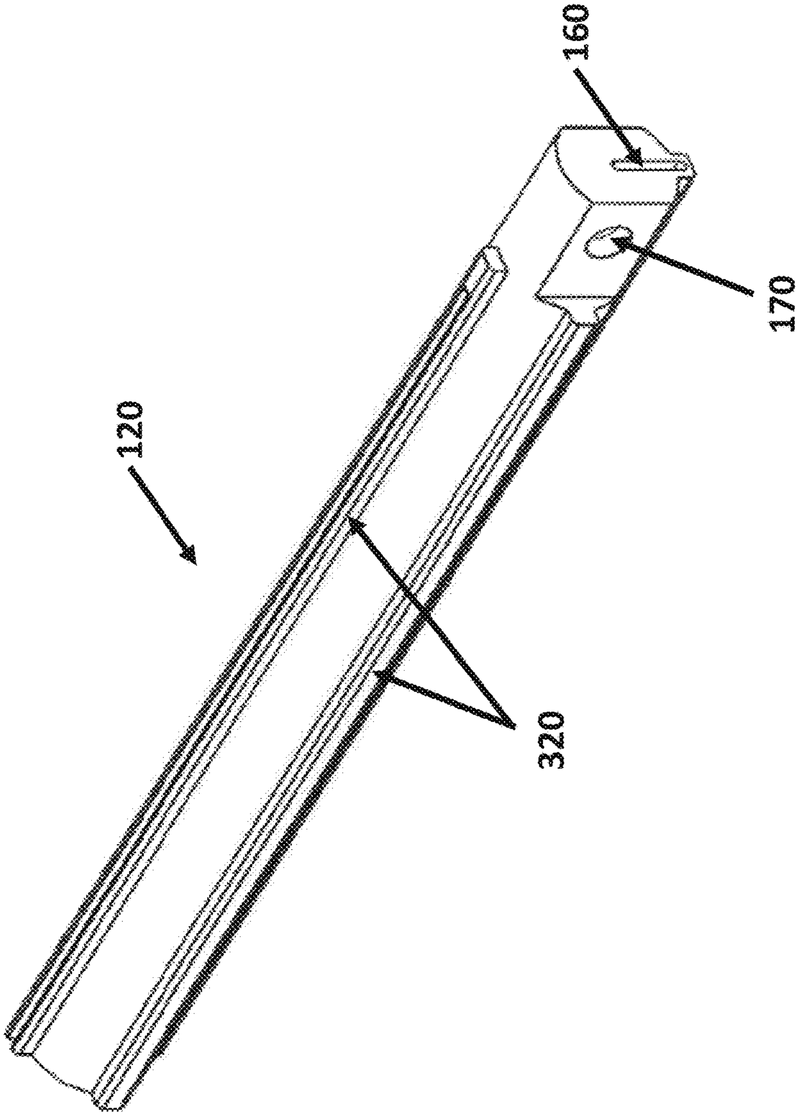
FIG. 5 shows an exemplary slider conduit of a needle bending device, according to one embodiment of the present disclosure.

FIG. 5 shows an exemplary embodiment of slider conduit 120. In this embodiment, the outer surface of slider conduit 120 comprises a plurality of ridges 320 to engage with base shaft 140. The internal dimension of slider conduit 120 is designed to allow needles of a variety of gauges to be disengaged following bending in such a manner to retain the bend. The distal end of slider conduit 120 comprises fulcrum 170 and aperture 160. The location of the bend is dictated by the location of fulcrum 170 along the shaft of needle 210. Aperture 160 is an opening in a capped distal end of the slider conduit 120 which allows the needle tip to exit slider conduit 120 and enter bending element 130. In this embodiment, aperture 160 extends halfway across the capped end of slider conduit 120. However, the aperture may be of any size or shape which allows needle 210 to enter and exit slider conduit 120 and bending element 130 before and after being bent. Alternatively, the distal end of slider conduit 120 may be open.

Figure 9B:
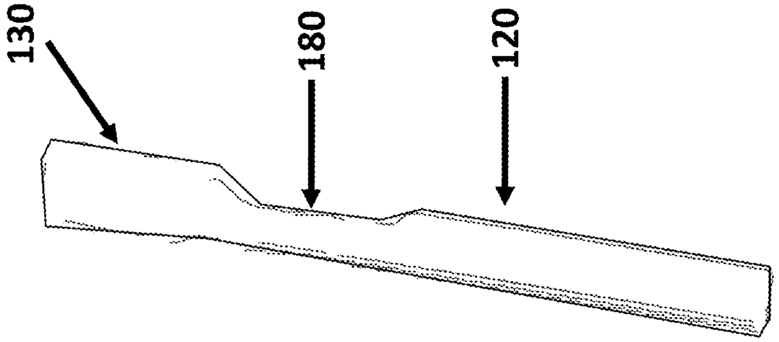
FIGS. 9A and 9B are representative images of exemplary slider conduits with corresponding bending elements, according to one embodiment of the present disclosure.
Figure 9A:
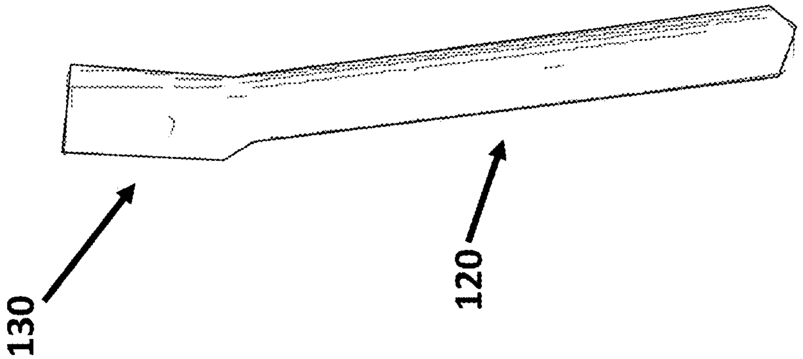
Figure 10A:
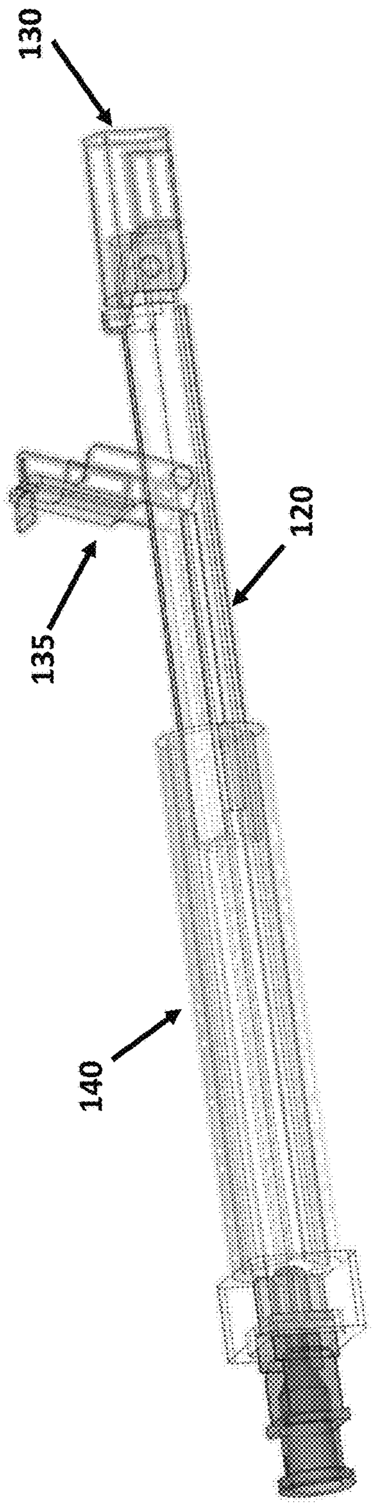
FIGS. 10A-10D show an exemplary needle bending device that includes a clamp that secures the distal portion of a needle in the device for subsequent bending, according to one embodiment of the present disclosure.
Figure 10B:
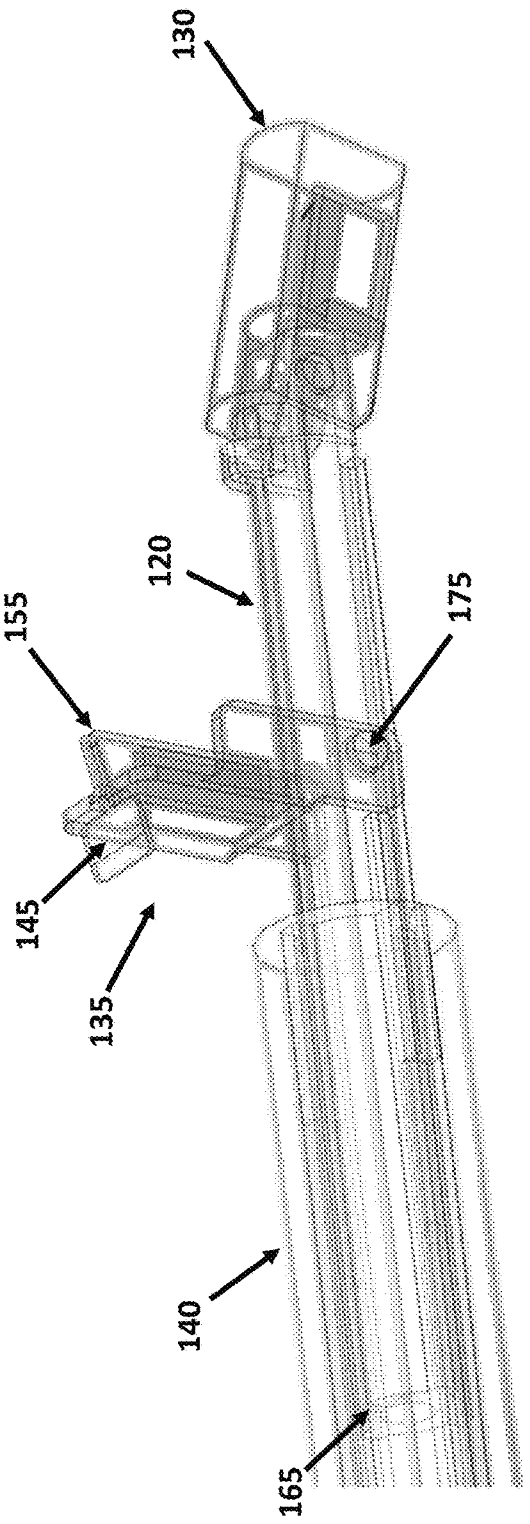
Figure 10C:
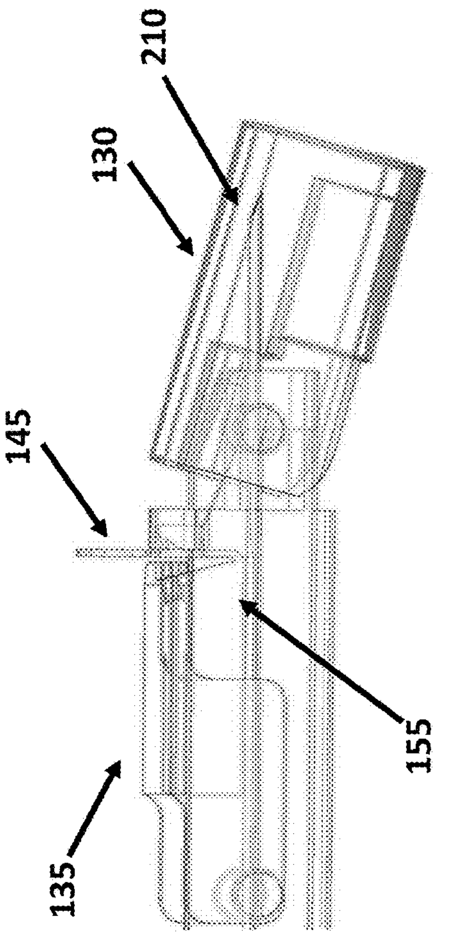
Figure 10D:
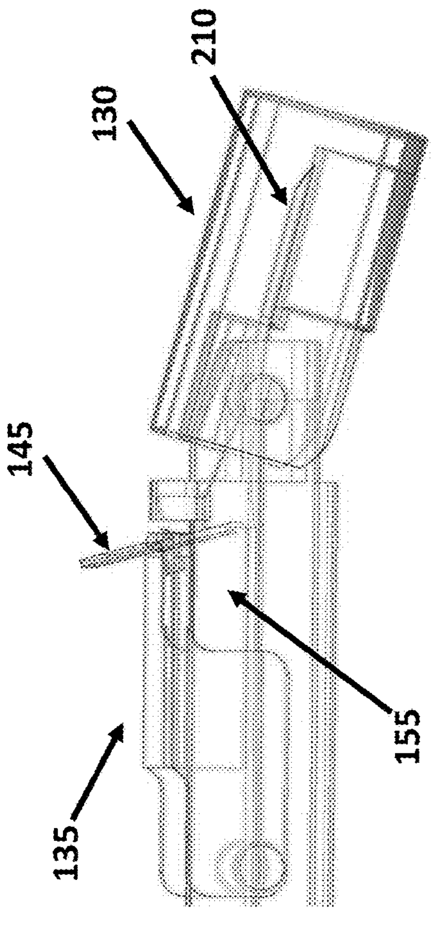

In alternative exemplary embodiments, slider conduit 120 comprises a slot running parallel along the length of slider conduit 120 and perpendicular from the outer surface to the internal chamber of slider conduit 120. In some embodiments, the slot facilitates facile removal of the needle from the device. Additionally, the distal end of slider conduit 120 may contain notch 180, as shown in FIG. 9B. The notch may receive a fingertip, or a press. A press may be a small piece of material (e.g., plastic, metal, or the like) with at least one flat surface able to be accommodated by the size of the notch. As such, the device may further comprise a press. Alternatively, slider conduit 120 may further comprise a hinged flap which covers notch. The fingertip, press, and hinged flap support the needle during bending.

Figure 6:
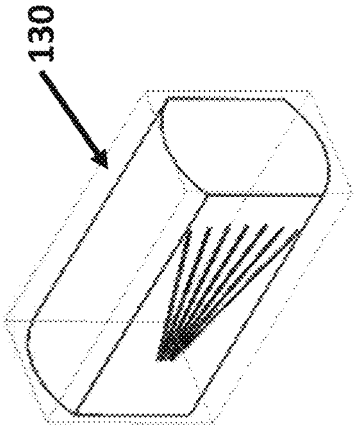
FIG. 6 shows an exemplary bending element of a needle bending device, according to one embodiment of the present disclosure.

FIG. 6 shows one embodiment of bending element 130. Bending element 130 may be semi-transparent, transparent, or have a viewing window to facilitate visualization of needle tip 220 during bending. Bending element 130 may have markers, gradations, or other similar indications of the degree of bend to allow the user to select desired angles. The device facilitates bends of less than or equal to 30 degrees (e.g., about 20 degrees, about 15 degrees, about 10 degrees, about 5 degrees). Alternatively, bending element 130 may be configured to bend the needle tip to a preset angle, for example 5 degrees.

FIG. 7 shows a cross-sectional view of one embodiment of bending element 130 engaged with slider conduit 120 during the process of bending needle 210. As described above, the combination of the bending element 130 and slider conduit 120 allows the user to bend needle 210 to a desired configuration or angle by applying pressure to the bending element 130 which in turn applies pressure to the portion of the needle remaining outside the slider conduit 120 to bend the needle along the shaft at 170. The user can bend the needle to a desired angle as determined by the markers, gradations, or other similar indications on the bending element 130. Needle tip 220 is protected within the bending element 130.

Figure 8:
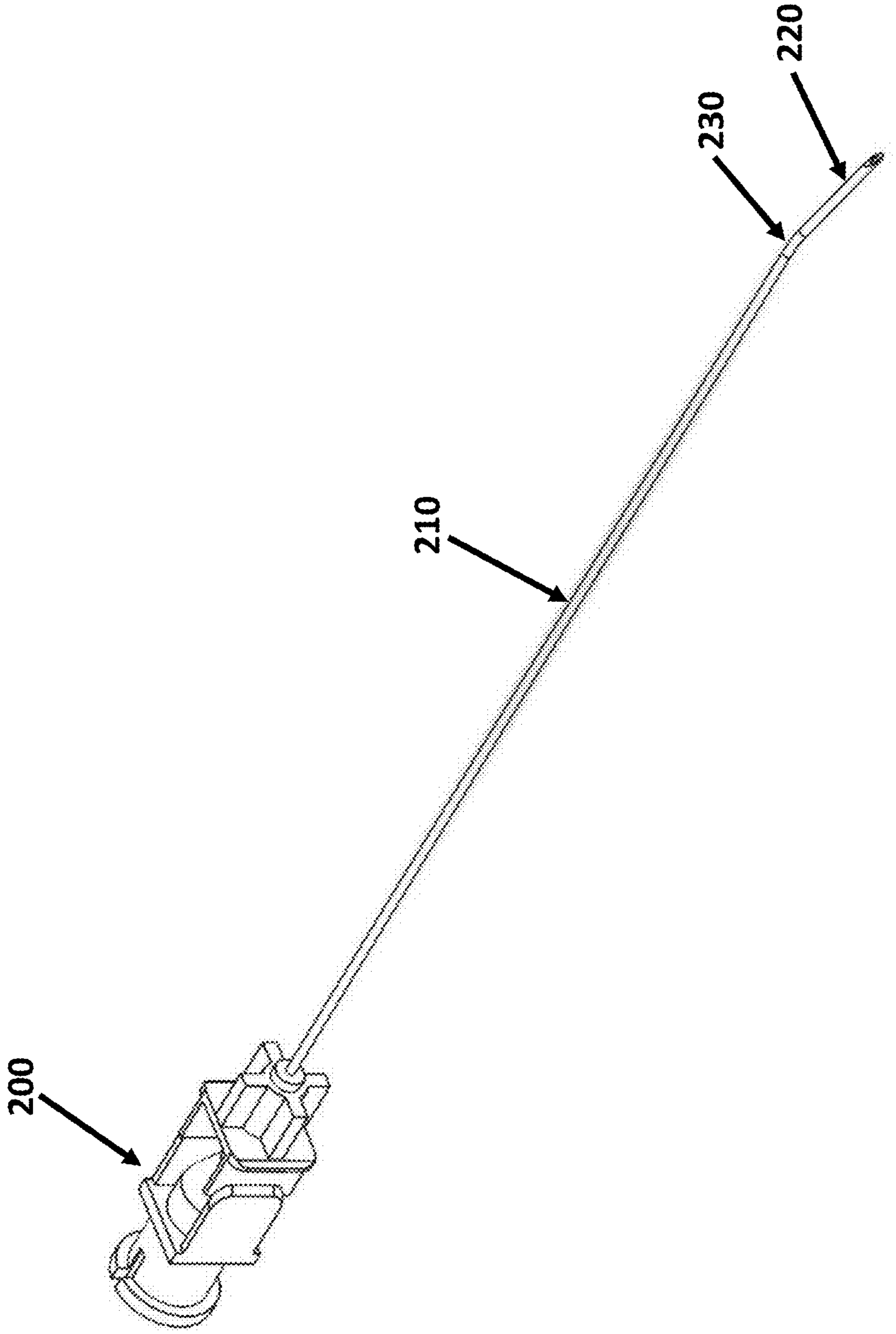
FIG. 8 shows an exemplary needle bent using a device as disclosed, according to one embodiment of the present disclosure.

FIG. 8 shows needle 210 following disengagement with the device (not shown). Needle 210 comprises bend 230 on the distal end of the shaft but proximal to needle tip 220. The needle can be attached to a syringe or other device at needle hub 200.

The device may further comprise a needle. The device may be used with any gauge of needle, with a preference for finer or higher gauge needles. In some embodiments, the gauge is between 20 and 26. In certain embodiments, the needle is 22 gauge or 25 gauge. The device can be used with any needle length ranging from 2 to 6 inches. The needle may be between 2 and 6 inches long. In certain embodiments, the needle is 3.5 inches long. In select embodiments, the needle is a spinal needle.

The devices of the present disclosure may be provided separately from a needle, and in some cases, in sterile packaging. The device may be supplied as part of a system and/or kit with or without a needle. The system or kit may further comprise a syringe or other device used for injection or removal of a sample (e.g., autoinjector, vial, tubing (e.g., catheter tubing)).

Individual components of the kits may be physically packaged together or separately, and in some cases, in sterile packaging. The components of the kit may be provided in multi-use or single-use amounts of the components. The kits can also comprise instructions for using the components of the kit. The instructions are relevant materials or methodologies pertaining to the kit. The materials may include any combination of the following: background information, list of components and their availability information (purchase information, etc.), brief or detailed protocols for using the compositions, trouble-shooting, references, technical support, and any other related documents. Instructions can be supplied with the kit or as a separate member component, either as a paper form or an electronic form which may be supplied on computer readable memory device or downloaded from an internet website, or as recorded presentation.

It is understood that the disclosed systems and kits can be employed in connection with the disclosed methods. The systems and kits may further contain containers, devices, or compositions for use with the methods employing the kit or using a bent needle, for example, imaging equipment, dyes or dye composition, and the like.

Also disclosed herein are methods of using the device disclosed herein to bend a needle. The needle may be bent by actuating the needle bending element to a desired angle. The desired angle for the needle bend is less than or equal to 30 degrees (e.g., about 20 degrees, about 15 degrees, about 10 degrees, about 5 degrees). The method may further comprise at least one or all of positioning the hollow slider conduit within the base, positioning the needle bending element over at least a portion of the hollow slider conduit at a distal end, and disengaging needle from the needle bending element, the hollow slider conduit, and the base simultaneously or sequentially. In those embodiments in which the device is supplied without a needle, the method further comprises inserting the needle into the base and securing a needle hub in the needle hub housing.

Figure 12A:
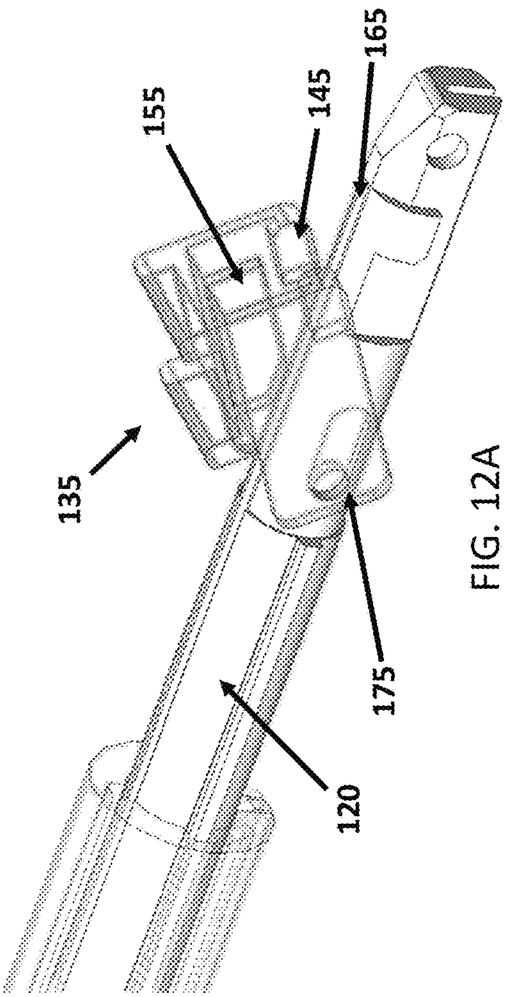
FIGS. 12A-12B show an exemplary needle bending device that includes a clamp that secures the distal portion of a needle in the device for subsequent bending, according to one embodiment of the present disclosure.
Figure 12B:
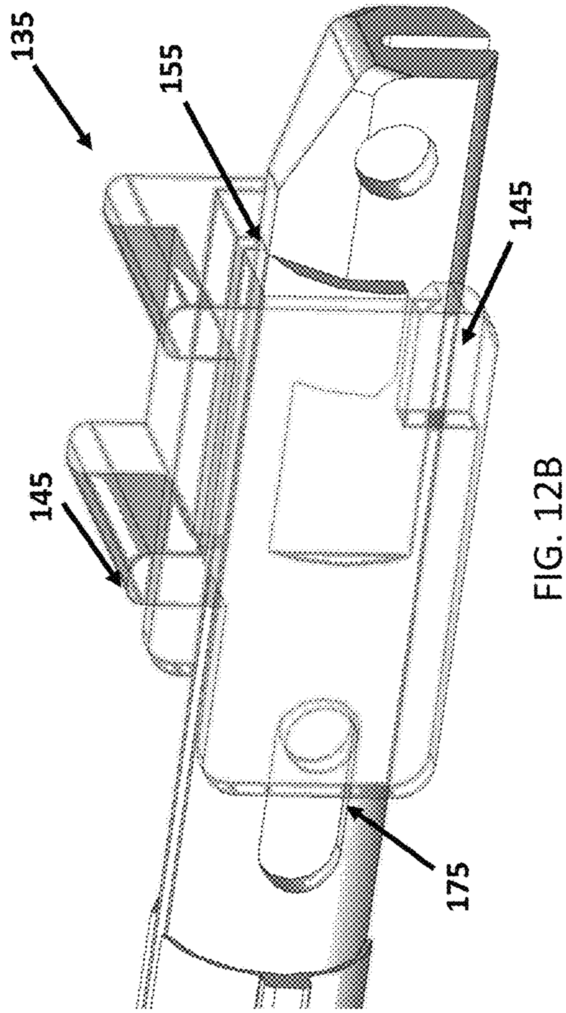

Embodiments of the present disclosure also include a needle bending device that includes a clamp that engages the needle and obviates the need to apply finger pressure to the needle when in operation. As shown in FIGS. 10A-10D, clamp 135 is functionally coupled to slider conduit 120 such that it can pivot up and down, or slide forward and backward along slider conduit 120 to engage the needle (FIGS. 12A-12B). Clamp 135 includes a latch or latching mechanism 145, which allows clamp 135 to engage a portion of slider conduit 120 and hold the needle in a substantially secure position when it is being bent by a user.

Clamp 135 also includes a clamping element 155 that bisects clamp 135 in a longitudinal manner. Clamping element 155 is configured to enter a slot 165 in the top portion of slider conduit 120, such that when clamp 135 is engaged against with the slider conduit 120, clamping element 155 contacts the needle and holds it in a substantially secure position while being bent by a user. The clamping element can be configured in any manner as long as it is able to enter and exit slot 165 and engage/disengage the needle. In some embodiments, the clamping element is generally solid but includes a groove along its center axis to allow for engagement with the needle. In other embodiments, the clamping element is bifurcated such that each of its two bifurcated sides engage the needle. Other configurations are also possible, as long as the clamping element engages the needle in a substantially secure manner. For example, in some embodiments, the surface of the clamping element that engages the needle can include a material that reduces friction and/or dampens vibrations, which can lessen stress on the needle during bending.

In general, as would be appreciated by one of ordinary skill in the art based on the present disclosure, clamp 135 and clamping element 155 can be detachably coupled to the slider conduit 120, or clamp 135 and clamping element 155 can be attached to the slider conduit 120 in a more or less permanent manner. In some embodiments, as shown in FIGS. 10A-10D, clamp 135 can be attached to the slider conduit 120 using a mechanism that allows for clamp 135 to pivot up (disengaged position) and down (engaged position) relative to slider conduit 120. FIGS. 10A-10D provide an exemplary structure of a clamp 135 that is attached to slider conduit 120 using two pivot screws 175 on either side of clamp 135.

In other embodiments, such as those shown in FIGS. 12A-12B, clamp 135 and clamping element 155 can be attached to slider conduit 120 using a mechanism that allows clamp 135 to pivot up and down as well as slide forward and backward along the longitudinal axis of slider conduit 120. FIGS. 12A-12B provide an exemplary slot structure 175 that includes a channel on either side of slider conduit 120 into which a peg can be inserted to allow backward (disengaged position) and forward (engaged position) movement relative to slider conduit 120. This mechanism can also include a latch or latching mechanism 145 (see also FIGS. 10A-10D) that allows clamp 135 to engage a complementary portion of slider conduit 120 and hold the needle in a substantially secure position when it is being bent by a user.

In accordance with these embodiments, the clamp and clamping element can be detachably coupled to the slider conduit to allow for a user to exchange one clamp for another. For example, in some cases, it may be advantageous to use different clamps to accommodate needles with different sizes, shapes, and/or gauges. In this manner, a user can exchange one clamp for another and bend needles with different sizes in a single procedure, which can reduce cost and improve efficiencies.

Figure 11A:
FIGS. 11A-11B show exemplary results of strain tests using the needle bending device of the present disclosure.
Figure 11B:
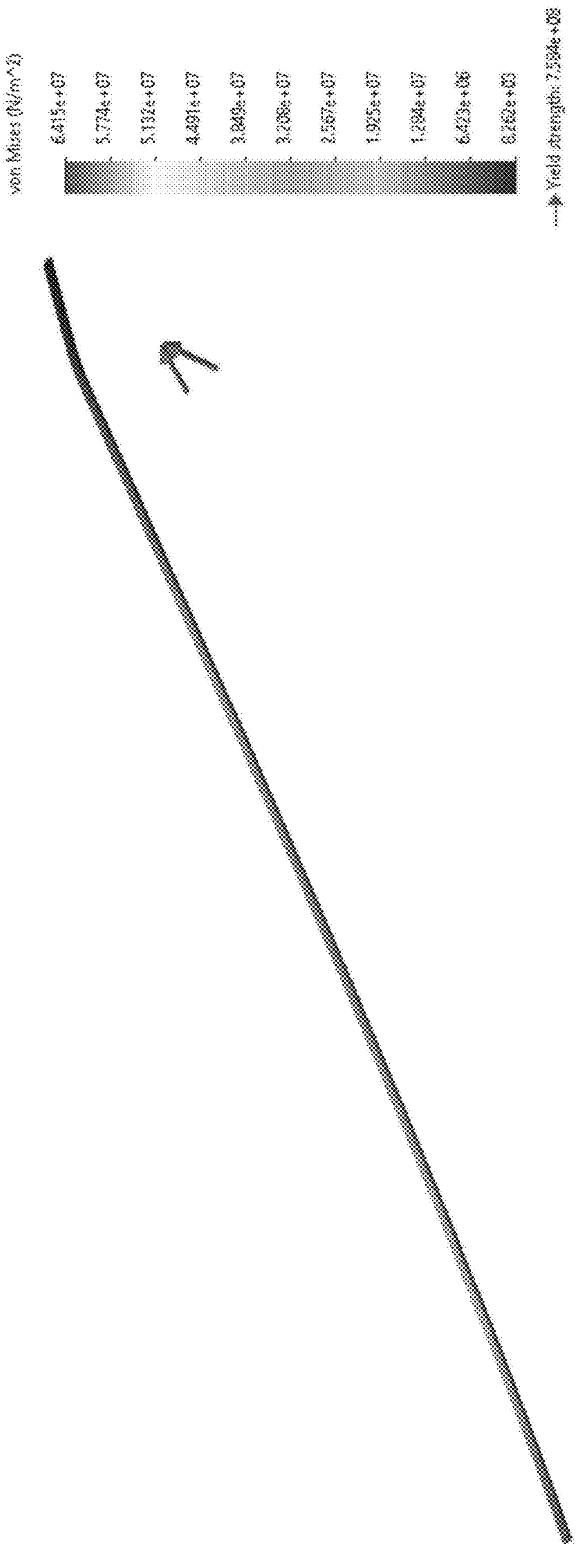

As shown in FIGS. 11A-11B, experiments were conducted to measure the stress and shape of a needle as it exits the slider conduit after bending. For example, one set of analyses was performed using a 25 gauge, 3.5" needle, with an O.D. of 0.5144 mm and I.D. of 0.260 mm. Bending forces were applied by the bending element 130, and the maximum tip length of the needle was 10 mm. For a post-bend deflection angle of about 5°, the tip displacement was 0.73 mm. For a post-bend deflection angle of about 15°, the tip displacement was 2.23 mm. Maximum elongation will occur at the 15° bend. The radius of curvature for the bent portion of the cannula was 12.75 mm. Assuming symmetric compression and elongation for the outer fibers, the elongation at the outside was 2.0%, which is well within the 7% maximum, which demonstrates that the structural integrity of the needle was intact after bending. Similarly, FIGS. 11A-11B show exemplary results of strain tests using the needle bending device of the present disclosure. FIG. 11A shows that a force of 0.01 N applied to the needle tip causes a deformation of 2.37 mm, while FIG. 11B shows that a force of 6,400,000 N/m of stress occurs at the base of the slider when the strain is set at 2.3 mm. This is less than 0.1 of the yield stress, which demonstrates that the needle can be removed from the slider conduit after bending without altering the bend created by the user.

Figure 13A:
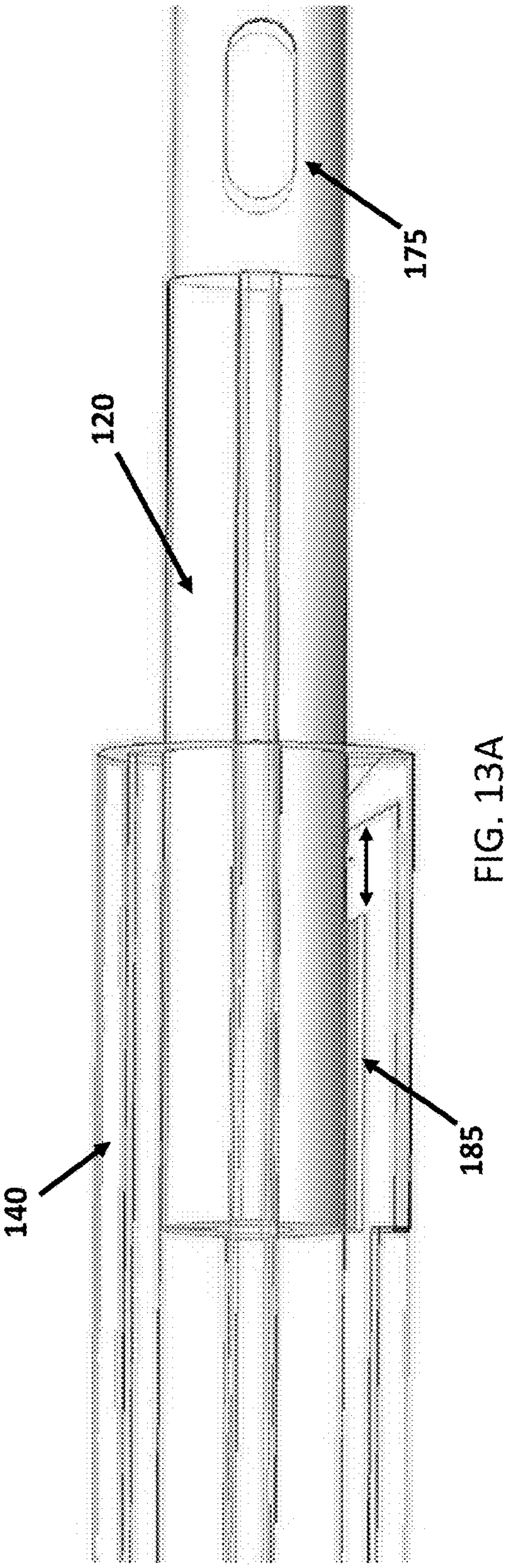
FIGS. 13A-13B show an exemplary needle bending device that includes a flange at the proximal end of the slider conduit that prevents it from fully exiting the distal end of the shaft, according to one embodiment of the present disclosure.
Figure 13B:
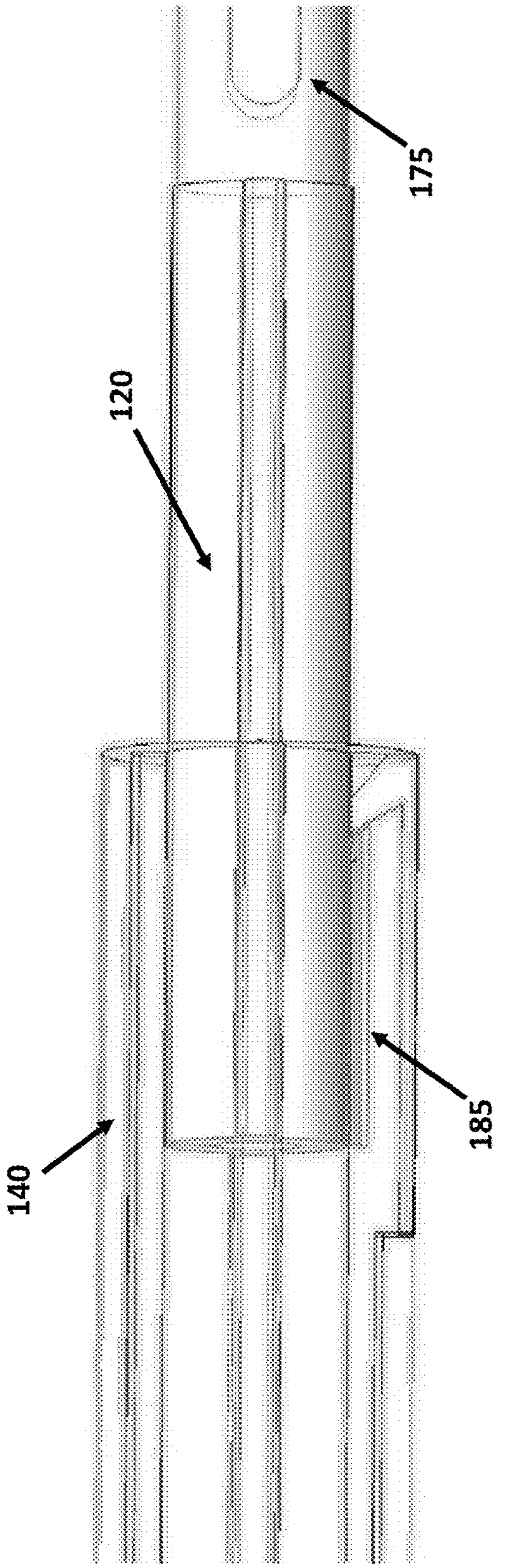

Embodiments of the present disclosure also include needle bending devices that comprise a mechanism that secures slider conduit 120 in position during use. For example, FIGS. 13A-13B show an exemplary needle bending device that includes a flange 185 at the proximal end of slider conduit 120 that prevents it from fully exiting the distal end of shaft 140. FIG. 13A provides a side view of flange 185 prior to engagement with the distal end of shaft 140 (see double arrow), while FIG. 13B provides a side view of flange 185 fully engaged against the distal end of shaft 140, which prevents it from exiting shaft 140. Slot 175 on the conduit slider 120 is also shown. Other configurations are also possible, as long as slider conduit 120 engages shaft 140 in a manner that prevents an unintentional release (e.g., release during needle bending) of slider conduit 120 from shaft 140.

It is understood that the foregoing detailed description and accompanying figures are merely illustrative and are not to be taken as limitations upon the scope of the disclosure, which is defined solely by the appended claims and their equivalents.

Various changes and modifications to the disclosed embodiments will be apparent to those skilled in the art and may be made without departing from the spirit and scope thereof.

We claim:

1. A needle bending device comprising:

a base;

a hollow slider conduit; and a bending element comprising an indication of bend angle.

2. The device of claim 1, wherein the base comprises a needle hub housing at a proximal end of a shaft.

3. The device of claim 2, wherein the needle hub housing is configured to receive a needle and engage a needle hub.

4. The device of claim 2, wherein the shaft comprises an elongated internal chamber configured to receive the hollow slider conduit from a distal end.

5. The device of claim 4, wherein the elongated internal chamber comprises one or more grooves on an interior surface to receive one or more ridges on an exterior surface of the hollow slider conduit.

6. The device of claim 1, wherein the hollow slider conduit has an open distal end.

7. The device of claim 1, wherein the hollow slider conduit has a closed distal end comprising an aperture.

8. The device of claim 1, wherein the hollow slider conduit comprises a slot running parallel along the length of the hollow slider conduit and perpendicular from the exterior surface to an internal chamber of slider conduit.

9. The device of claim 1, wherein the hollow slider conduit comprises a notch on the exterior surface proximal to the bending element.

10. The device of claim 9, wherein the hollow slider conduit comprises a hinged flap configured to be received in the notch.

11. The device of claim 10, further comprising a press.

12. The device of claim 1, wherein the hollow slider conduit comprises a fulcrum.

13. The device of claim 1, wherein the bending element engages with the hollow slider conduit at a distal end.

14. The device of claim 1, wherein the bending element is fully or partially transparent or semi-transparent.

15. The device of claim 1, wherein the bending element comprises an opening.

16. The device of claim 1, wherein the indication corresponds to a bend angle of less than or equal to 30 degrees.

17. The device of claim 1, wherein the indication corresponds to a bend angle of about 5 degrees.

18. A kit comprising:

the device of claim 1;

a needle; and a container.

19. A method comprising bending a needle using the device of claim 1.

20. A needle bending device comprising:

a base;

a hollow slider conduit comprising a fulcrum that provides a pivot point for bending a needle; and a bending element comprising an indication of bend angle and configured to apply force to bend a distal end of the needle at the fulcrum.

21. A method of bending a needle for a medical procedure, the method comprising:

positioning a needle within a hollow slider conduit of a needle bending device, the needle bending device comprising a base, the hollow slider conduit, and a bending element comprising an indication of bend angle;

selecting a desired bend angle using the indication of bend angle on the bending element; and applying force to the bending element to bend a distal end of the needle to the desired bend angle.

* * * * *